US012624115B2

(12) United States Patent
Dix et al.

(10) Patent No.: US 12,624,115 B2
(45) Date of Patent: \*May 12, 2026

(54) STABILIZED FORMULATIONS CONTAINING ANTI-INTERLEUKIN-4 RECEPTOR (IL-4R) ANTIBODIES

(71) Applicant: Regeneron Pharmaceuticals, Inc., Tarrytown, NY (US)

(72) Inventors: Daniel B. Dix, LaGrangeville, NY (US); Xiaolin Tang, Old Tappan, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/333,265

(22) Filed: Sep. 18, 2025

(65) Prior Publication Data

US 2026/0022183 A1      Jan. 22, 2026

Related U.S. Application Data

(63) Continuation of application No. 18/432,780, filed on Feb. 5, 2024, which is a continuation of application No. 17/342,949, filed on Jun. 9, 2021, now Pat. No. 11,926,670, which is a continuation of application No. 16/543,832, filed on Aug. 19, 2019, now Pat. No. 11,059,896, which is a continuation of application No. 15/424,578, filed on Feb. 3, 2017, now Pat. No. 10,435,473, which is a continuation of application No. 14/963,712, filed on Dec. 9, 2015, now abandoned, which is a continuation of application No. 14/578,179, filed on Dec. 19, 2014, now Pat. No. 9,238,692, which is a continuation of application No. 13/253,103, filed on Oct. 5, 2011, now Pat. No. 8,945,559.

(60) Provisional application No. 61/390,283, filed on Oct. 6, 2010.

(51) Int. Cl.
| | |
|---|---|
| *C07K 16/28* | (2006.01) |
| *A61K 9/00* | (2006.01) |
| *A61K 39/395* | (2006.01) |
| *A61K 47/18* | (2017.01) |
| *A61M 5/315* | (2006.01) |

(52) U.S. Cl.
CPC ........ *C07K 16/2866* (2013.01); *A61K 9/0019* (2013.01); *A61K 39/39591* (2013.01); *A61K 47/183* (2013.01); *A61M 5/315* (2013.01); *C07K 2317/21* (2013.01); *C07K 2317/56* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,171,586 | B1 | 1/2001 | Lam et al. |
| 7,186,809 | B2 | 3/2007 | Pluenneke |
| 7,303,748 | B2 | 12/2007 | Wiegand |
| 7,465,450 | B2 | 12/2008 | Pluenneke |
| 7,605,237 | B2 | 10/2009 | Stevens et al. |
| 7,608,261 | B2 | 10/2009 | Furfine et al. |
| 7,608,693 | B2 | 10/2009 | Martin et al. |
| 8,075,887 | B2 | 12/2011 | Martin et al. |
| 8,337,839 | B2 | 12/2012 | Martin et al. |
| 8,372,396 | B2 | 2/2013 | Andya et al. |
| 8,945,559 | B2 | 2/2015 | Dix et al. |
| 9,238,692 | B2 | 1/2016 | Dix et al. |
| 10,435,473 | B2 | 10/2019 | Dix et al. |
| 11,059,896 | B2 | 7/2021 | Dix et al. |
| 11,926,670 | B2 | 3/2024 | Dix et al. |
| 12,042,538 | B2 | 7/2024 | Patel et al. |
| 2006/0217311 | A1 | 9/2006 | Dix et al. |
| 2010/0015157 | A1 | 1/2010 | Andya et al. |
| 2010/0021476 | A1 | 1/2010 | Stevens et al. |
| 2010/0047254 | A1 | 2/2010 | Martin et al. |
| 2010/0278822 | A1 | 11/2010 | Fraunhofer et al. |
| 2011/0171241 | A1 | 7/2011 | Dix et al. |
| 2013/0078675 | A1 | 3/2013 | Martin et al. |
| 2014/0056920 | A1 | 2/2014 | Ardeleanu et al. |
| 2014/0072583 | A1 | 3/2014 | Ardeleanu et al. |
| 2016/0102147 | A1 | 4/2016 | Dix et al. |

FOREIGN PATENT DOCUMENTS

| | | | |
|---|---|---|---|
| EP | 1314437 | A1 | 5/2003 |
| WO | 04/091658 | A1 | 10/2004 |
| WO | 06/138181 | A2 | 12/2006 |
| WO | 09/009406 | A1 | 1/2009 |

(Continued)

OTHER PUBLICATIONS

Abe, "Role of Histidine-Related Compounds as Intracellular Proton Buffering Constituents in Vertebrate Muscle," Biochemistry (Moscow), vol. 65, No. 7, 2000, pp. 757-765. Translated from Biokhimiya, vol. 65, No. 7, pp. 891-900. (2000).

(Continued)

*Primary Examiner* — Ruixiang Li

(74) *Attorney, Agent, or Firm* — Schwabe, Williamson & Wyatt PC; Lisa Dornbach Flanagan

(57) ABSTRACT

The present invention provides pharmaceutical formulations comprising a human antibody that specifically binds to human interleukin-4 receptor (hIL-4R). The formulations may contain, in addition to an anti-hIL-4R antibody, at least one amino acid, at least one sugar, or at least one non-ionic surfactant. The pharmaceutical formulations of the present invention exhibit a substantial degree of antibody stability after storage for several months.

30 Claims, No Drawings

Specification includes a Sequence Listing.

(56) References Cited

FOREIGN PATENT DOCUMENTS

| WO | 10/042705 A1 | 4/2010 |
| WO | 10/053751 A1 | 5/2010 |
| WO | 10/102241 A1 | 9/2010 |
| WO | 12/047954 A1 | 1/2012 |
| WO | 12/065072 A2 | 5/2012 |
| WO | 13/131866 A1 | 9/2013 |
| WO | 15/159254 A1 | 10/2015 |

OTHER PUBLICATIONS

Christensen et al., "Current Concepts of Acid-Base Measurement," Annals of the New York Academy of Sciences, vol. 133, Art. 1, pp. 1-274, (1966).

Daugherty et al., "Formulation and delivery issues for monoclonal antibody therapeutics," Adv. Drug Delivery Reviews, 58:686-706, (2006).

Doshi et al., "A Comprehensive Assessment of All-Oleate Polysorbate 80: Free Fatty Acid Particle Formation, Interfacial Protection and Oxidative Degradation," Pharm Res (2021) 38:531-548. [https://doi.org/10.1007/s11095-021-03021-z].

Gokarn et al., "Self-buffering Antibody Formulations," Journal of Pharmaceutical Sciences, 97(8):3051-3066, (2008).

Nozaki et al., "Methods in Enzymology vol. XI: Enzyme Structure," Academic Press New York and London, Library of Congress Catalog Card No. 54-9110, (1967).

Patro et al., "Protein formulation and fill-finish operations," Biotechnol Annu Rev, 8:55-84, (2002). Abstract only.

Pegues et al., "Effect of Fatty Acid Composition in Polysorbate 80 on the Stability of Therapeutic Protein Formulations," Pharm Res (2021) 38:1961-1975.

Takahiko Ito et al., "Effects of subclass change on the structural stability of chimeric, humanized, and human antibodies under thermal stress: Subclass Change and Antibody Thermal Stability," Protein Science, vol. 22(No. 11): Nov. 1, 2013; pp. 1542-1551, XP55410767.

Roy et al., "Polysorbate Degradation and Particle Formation in a High Concentration mAb: Formulation Strategies to Minimize Effect of Enzymatic Polysorbate Degradation," Journal of Pharmaceutical Sciences 110 (2021) 3313-3323. [https://doi.org/10.1016/j.xphs.2021.05.012].

Wang et al., "Minireview: Antibody Structure, Instability, and Formulation," Journal of Pharmaceutical Sciences, 96(1):1-26, (2007).

Wang, "Instability, stabilization, and formulation of liquid protein pharmaceuticals," Int'l J. Pharmaceutics, 185(2):129-188, (1999).

Wang et al., "Stabilizing two IgG1 monoclonal antibodies by surfactants: Balance between aggregation prevention and structure perturbation," Science Direct: European Journal of Pharmaceutics and Biopharmaceutics, vol. 114: 263-277 (2017). [http://dx.doi.org/10.1016/j.ejpb.2017.01.025].

Wang et al., "Stabilizing two IgG1 monoclonal antibodies by surfactants: Balance between aggregation prevention and structure perturbation," European Journal of Pharmaceutics and Biopharmaceutics, vol. 114: 263-277, (2017). [http://dx.doi.org/10.1016/j.ejpb.2017.01.025].

Wyman, "An Analysis of the Titration Data of Oxyhemoglobin of the Horse by a Thermal Method," Biological Laboratories, Harvard University, Cambridge, pp. 1-13, (1939).

U.S. Appl. No. 13/253,103, Final Office Action mailed Apr. 22, 2014.

U.S. Appl. No. 13/253,103, Non-Final Office Action mailed Nov. 4, 2013.

U.S. Appl. No. 13/253,103, Notice of Allowance mailed Sep. 25, 2014.

U.S. Appl. No. 14/578,179, Non-Final Office Action mailed Feb. 5, 2015.

U.S. Appl. No. 14/578,179, Notice of Allowance mailed Sep. 9, 2015.

U.S. Appl. No. 14/963,712, Final Office Action mailed Aug. 5, 2016.

U.S. Appl. No. 14/963,712, Non-Final Office Action mailed Jan. 25, 2016.

U.S. Appl. No. 15/424,578, Non-Final Office Action mailed Nov. 20, 2017.

U.S. Appl. No. 15/424,578, Final Office Action mailed Jun. 12, 2018.

U.S. Appl. No. 15/424,578, Notice of Allowance mailed May 17, 2019.

U.S. Appl. No. 16/543,832, Non-Final Office Action mailed May 20, 2020.

U.S. Appl. No. 16/543,832, Final Office Action mailed Sep. 9, 2020.

U.S. Appl. No. 16/543,832, Notice of Allowance mailed Mar. 10, 2021.

U.S. Appl. No. 17/342,949, Non-Final Office Action mailed Mar. 15, 2023.

U.S. Appl. No. 17/342,949, Final Office Action mailed Jul. 26, 2023.

U.S. Appl. No. 17/342,949, Notice of Allowance mailed Nov. 6, 2023.

WIPO Application No. PCT/US2011/054856, PCT International Preliminary Report on Patentability mailed Apr. 18, 2013.

WIPO Application No. PCT/US2011/054856, PCT International Search Report mailed Mar. 29, 2012.

WIPO Application No. PCT/US2023/020660, PCT International Search Report and Written Opinion of the International Searching Authority mailed Aug. 1, 2023.

STABILIZED FORMULATIONS CONTAINING ANTI-INTERLEUKIN-4 RECEPTOR (IL-4R) ANTIBODIES

CROSS-REFERENCE TO RELATED APPLICATIONS

This application is a continuation of U.S. application Ser. No. 18/432,780, filed Feb. 5, 2024, which is a continuation of U.S. application Ser. No. 17/342,949, filed Jun. 9, 2021, now U.S. Pat. No. 11,926,670, which is a continuation of U.S. application Ser. No. 16/543,832, filed Aug. 19, 2019, now U.S. Pat. No. 11,059,896, which is a continuation of U.S. application Ser. No. 15/424,578, filed Feb. 3, 2017, now U.S. Pat. No. 10,435,473, which is a continuation of U.S. application Ser. No. 14/963,712, filed Dec. 9, 2015, which is a continuation of U.S. application Ser. No. 14/578, 179, filed Dec. 19, 2014, now U.S. Pat. No. 9,238,692, which is a continuation of U.S. application Ser. No. 13/253, 103, filed Oct. 5, 2011, now U.S. Pat. No. 8,945,559, which claims the benefit of priority under 35 U.S.C. § 119 (e) of U.S. Provisional Application No. 61/390,283, filed Oct. 6, 2010, each of which is herein incorporated by reference in its entirety.

SEQUENCE LISTING

This application incorporates by reference a computer readable Sequence Listing in ST.26 XML format, titled 6032US09_Sequence, created on Sep. 18, 2025, and containing 23,111 bytes.

FIELD

The present invention relates to the field of therapeutic antibody formulations. More specifically, the present invention relates to the field of pharmaceutical formulations comprising a human antibody that specifically binds to human interleukin-4 receptor.

BACKGROUND

Therapeutic macromolecules (e.g., antibodies) must be formulated in a manner that not only makes the molecules suitable for administration to patients, but also maintains their stability during storage and subsequent use. For example, therapeutic antibodies in liquid solution are prone to degradation, aggregation or undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation, and the visual quality or appeal of the formulation. Thus, when formulating a therapeutic antibody, great care must be taken to arrive at a formulation that remains stable, contains an adequate concentration of antibody, and possesses a suitable viscosity as well as other properties which enable the formulation to be conveniently administered to patients.

Antibodies to the human interleukin-4 receptor alpha (hIL-4Rα) are one example of a therapeutically relevant macromolecule that requires proper formulation. Anti-hIL- 4Rα antibodies are clinically useful for the treatment or prevention of diseases such as atopic dermatitis and allergic asthma, and other conditions. Exemplary anti-IL-4Rα antibodies are described, inter alia, in U.S. Pat. Nos. 7,605,237; 7,608,693; 7,465,450; and 7,186,809; and US Patent Applications No. 2010-0047254 and 2010-0021476.

Although anti-hIL-4Rα antibodies are known, there remains a need in the art for novel pharmaceutical formulations comprising anti-hIL-4Rα antibodies which are sufficiently stable and suitable for administration to patients.

SUMMARY

The present invention satisfies the aforementioned need by providing pharmaceutical formulations comprising a human antibody that specifically binds to human interleukin-4 receptor alpha (hIL-4Rα).

In one aspect, a liquid pharmaceutical formulation is provided, comprising: (i) a human antibody that specifically binds to human interleukin-4 receptor alpha (hIL-4Rα); (ii) a buffer; (iii) an organic cosolvent; (iv) a thermal stabilizer; and (v) a viscosity reducer.

In one embodiment, the antibody is provided at a concentration of about 150 mg/ml±50 mg/ml. In another embodiment, the antibody is provided at a concentration of about 150 mg/ml±15 mg/ml. In a specific embodiment, the antibody is provided at a concentration of about 150 mg/ml.

In one embodiment, the antibody comprises any one or more of an amino acid sequence of SEQ ID NO:1-8. In one embodiment, the antibody comprises (a) a heavy chain variable region (HCVR) comprising heavy chain complementarity determining regions 1, 2 and 3 (HCDR1-HCDR2-HCDR3) each comprising a sequence of SEQ ID NO:2, SEQ ID NO:3 and SEQ ID NO:4, respectively; and (b) a light chain variable region (LCVR) comprising light chain complementarity determining regions 1, 2 and 3 (LCDR1-LCDR2-LCDR3) each comprising a sequence of SEQ ID NO:6, SEQ ID NO:7 and SEQ ID NO:8, respectively. In a specific embodiment, the antibody comprises an HCVR and an LCVR, each of which comprises the amino acid sequence of SEQ ID NO:1 and SEQ ID NO:5, respectively.

In one embodiment, the antibody comprises any one or more of an amino acid sequence of SEQ ID NO:9-16. In one embodiment, the antibody comprises (a) a heavy chain variable region (HCVR) comprising heavy chain complementarity determining regions 1, 2 and 3 (HCDR1-HCDR2-HCDR3) each comprising a sequence of SEQ ID NO:10, SEQ ID NO:11 and SEQ ID NO:12, respectively; and (b) a light chain variable region (LCVR) comprising light chain complementarity determining regions 1, 2 and 3 (LCDR1-LCDR2-LCDR3) each comprising a sequence of SEQ ID NO:14, SEQ ID NO:15 and SEQ ID NO:16, respectively. In a specific embodiment, the antibody comprises an HCVR and an LCVR, each of which comprises the amino acid sequence of SEQ ID NO:9 and SEQ ID NO:13, respectively.

In one embodiment, the antibody comprises any one or more of an amino acid sequence of SEQ ID NO:17-24. In one embodiment, the antibody comprises (a) a heavy chain variable region (HCVR) comprising heavy chain complementarity determining regions 1, 2 and 3 (HCDR1-HCDR2-HCDR3) each comprising a sequence of SEQ ID NO:18, SEQ ID NO:19 and SEQ ID NO:20, respectively; and (b) a light chain variable region (LCVR) comprising light chain complementarity determining regions 1, 2 and 3 (LCDR1-LCDR2-LCDR3) each comprising a sequence of SEQ ID NO:22, SEQ ID NO:23 and SEQ ID NO:24, respectively. In a specific embodiment, the antibody comprises an HCVR and an LCVR, each of which comprises the amino acid sequence of SEQ ID NO:17 and SEQ ID NO:21, respectively.

In one embodiment, the pH of the liquid formulation is about pH 5.9±0.5. In a specific embodiment, the pH of the liquid formulation is about pH 5.9±0.1. In one embodiment, the liquid pharmaceutical buffer comprises one or more buffers, which can buffer from about pH 5.6 to about pH 6.2.

In one embodiment, the liquid pharmaceutical formulation comprises a buffer system that comprises at least two buffers. In one embodiment, the buffer system comprises a first buffer having an effective pH range within 3.6-5.6 and a second buffer having an effective pH range within 5.5-7.4. In one embodiment, the first buffer has a pKa of about 4.8±0.3 and the second buffer has a pKa of about 6.0±0.3. In a specific embodiment, the first buffer is an acetate buffer and the second buffer is a histidine buffers. In one specific embodiment, the acetate is at a concentration of 12.5 mM±1.9 mM and the histidine is at a concentration of 20 mM±3 mM.

In one embodiment, the organic cosolvent is a nonionic polymer containing a polyoxyethylene moiety. In some embodiments, the organic cosolvent is any one or more of polysorbate 20, poloxamer 181 and polyethylene glycol 3350. In a specific embodiment, the organic copolymer is polysorbate 20.

In one embodiment, the organic cosolvent is at a concentration of from about 0.2%±0.03% to about 1%±0.15% "weight to volume" or "w/v", wherein, e.g., 0.1 g/ml=10% and 0.01 g/ml=1%). In a specific embodiment, the organic cosolvent is polysorbate 20, which is at a concentration of about 0.2%±0.03% w/v.

In one embodiment, the thermal stabilizer is a sugar. In one embodiment, the sugar is selected from the group consisting of sucrose, mannitol and trehalose. In a specific embodiment, the thermal stabilizer is sucrose.

In one embodiment, the thermal stabilizer is at a concentration of from about 0.9%±0.135% w/v to about 10%±1.5% w/v. In a specific embodiment, the thermal stabilizer is sucrose at a concentration of about 5%±0.75% w/v.

In one embodiment, the viscosity reducer is a salt selected from the group consisting of arginine hydrochloride, sodium thiocyanate, ammonium thiocyanate, ammonium sulfate, ammonium chloride, calcium chloride, zinc chloride and sodium acetate. In a specific embodiment, the viscosity reducer is L-arginine hydrochloride.

In one embodiment, the viscosity reducer is at a concentration that is not more than 100 mM. In one embodiment, the viscosity reducer is at a concentration of 50 mM±7.5 mM. In another embodiment, the viscosity reducer is at a concentration of 25 mM±3.75 mM. In a specific embodiment, the viscosity reducer is 25 mM±3.75 mM L-arginine hydrochloride.

In one embodiment, the viscosity of the liquid pharmaceutical formulation is less than or equal to about 35±3.5 cPoise. In one embodiment, the viscosity is about 21.5±13.5 cPoise, about 11±1.1 cPoise or about 8.5±0.85 cPoise. In a specific embodiment, the viscosity of the liquid pharmaceutical formulation is about 8.5±0.85 cPoise.

In one embodiment, the osmolality of the liquid pharmaceutical formulation is less than about 450 mOsm/kg. In one embodiment, the osmolality of the liquid pharmaceutical formulation is about 290±20 mOsm/kg.

In one embodiment, at least 90% or at least 95% of the native form of the anti-hIL-4Rα antibody is recovered from the liquid pharmaceutical formulation after six months of storage of the liquid pharmaceutical formulation at 5° C., as determined by size exclusion chromatography.

In a specific embodiment, at least 98% of the native form of the antibody is recovered after six months of storage at 5° C., as determined by size exclusion chromatography.

In one embodiment, at least 90% of the native form of the antibody is recovered from the liquid pharmaceutical formulation after eight weeks of storage at 45° C., as determined by size exclusion chromatography.

In one embodiment, less than 45% of the antibody, which is recovered from the liquid pharmaceutical formulation after eight weeks of storage at 45° C., is an acidic form, as determined by cation exchange chromatography.

In one embodiment, less than about 4% of the antibody, which is recovered from the liquid pharmaceutical formulation after six months of storage at 25° C., is aggregated, as determined by size exclusion exchange chromatography.

In one aspect, a liquid pharmaceutical formulation is provided, comprising: (i) about 150 mg/ml±50 mg/ml of a human antibody that specifically binds to hIL-4Rα, wherein the antibody comprises a heavy chain variable region (HCVR) and light chain variable region (LCVR) comprising an amino acid sequence of SEQ ID NO:1 and SEQ ID NO:5, respectively; (ii) about 12.5 mM±2 mM acetate; (iii) about 20 mM±3 mM histidine; (iv) about 5%±0.75% (w/v) sucrose; (v) about 0.2%±0.03% (w/v) polysorbate 20; and (vi) about 25 mM±3.75 mM arginine, at a pH of about 5.9±0.5.

In one embodiment, the liquid pharmaceutical formulation has a viscosity of from about 8.5±0.85 cPoise to about 11±1.1 cPoise. In a specific embodiment, the viscosity of the liquid pharmaceutical formulation is about 8.5±0.85 cPoise.

In one embodiment, the liquid pharmaceutical formulation is physiologically isotonic. In one embodiment, the osmolality of the liquid pharmaceutical formulation is about 290±20 mOsm/kg.

In one embodiment, at least about 98% of the native form of the anti-hIL4-Rα antibody is recovered from the liquid pharmaceutical formulation after six months of storage at 5° C., as determined by size exclusion chromatography.

In one embodiment, at least about 90% of the native form of the anti-hIL4-Rα antibody is recovered from the liquid pharmaceutical formulation after eight weeks of storage at 45° C., as determined by size exclusion chromatography.

In one embodiment, less than about 45% of the antibody, which is recovered from the liquid pharmaceutical formulation after eight weeks of storage at 45° C., is an acidic form, as determined by cation exchange chromatography.

In one embodiment, less than 4% of the antibody, which is recovered from the liquid pharmaceutical formulation after six months of storage at 25° C., is aggregated, as determined by size exclusion exchange chromatography.

In one aspect, a stable low viscosity isotonic liquid pharmaceutical formulation, which contains at least 100 mg/ml of a stable anti-hIL4-Rα antibody, is provided. In one embodiment, the antibody is at a concentration of about 150 mg/ml±50 mg/ml. In a specific embodiment, the antibody concentration is about 150 mg/ml±15 mg/ml.

In one embodiment, the antibody comprises any one or more of an amino acid sequence of SEQ ID NO:1-8. In one embodiment, the antibody comprises a heavy chain variable region (HCVR) and a light chain variable region (LCVR), wherein the HCVR/LCVR combination comprises heavy and light chain complementarity determining regions (HCDR1-HCDR2-HCDR3/LCDR1-LCDR2-LCDR3), which comprise the amino acid sequences of SEQ ID NOs: 2-3-4/SEQ ID NOs: 6-7-8, respectively. In a specific embodiment, the antibody comprises an HCVR and an LCVR, each of which comprises the amino acid sequence of SEQ ID NO: 1 and SEQ ID NO:5, respectively.

In some embodiments, the formulation has a viscosity of less than 35±3.5 cPoise, less than 20±2 cPoise, less than 15±1.5 cPoise, or less than 10±1 cPoise. In a specific embodiment, the liquid formulation has a viscosity of about 8.5±2.5 cPoise.

In one embodiment, the formulation has an osmolarity that is physiologically compatible. In a specific embodiment, the formulation comprises an osmolality of 290±20 mOsm/kg.

In one embodiment, the antibody is stable for at least about six months at about 5° C. In a specific embodiment, at least about 98% of the antibody retains its native conformation at about six months of storage at 5° C., as determined by size exclusion chromatography.

In one embodiment, the antibody is stable for at least about eight weeks of storage at about 45° C. In a specific embodiment, at least about 90% of the antibody retains its native conformation at about eight weeks of storage at 45° C., as determined by size exclusion chromatography. In a specific embodiment, less than about 45% of the antibody comprises an acidic form at about eight weeks of storage at 45° C., as determined by cation exchange chromatography.

In one embodiment, the antibody is stable for at least about six months of storage at about 25° C. In a specific embodiment, less than about 4% of the antibody comprises an aggregated form at about six months of storage at 25° C., as determined by size exclusion chromatography.

In one embodiment, the formulation comprises a buffer and has a pH of about pH 5.9±0.5. In one embodiment, the buffer comprises an acetate buffer and a histidine buffer. In a specific embodiment, the acetate is at a concentration of 12.5 mM±1.9 mM and the histidine is at a concentration of 20 mM±3 mM.

In one embodiment, the formulation comprises an organic cosolvent at a concentration of from about 0.2%±0.03% to about 1%±0.15% w/v. In one embodiment, the organic cosolvent is a nonionic polymer containing a polyoxyethylene moiety. In some embodiments, the organic cosolvent is any one or more of polysorbate 20, poloxamer 181 and polyethylene glycol 3350. In a specific embodiment, the organic cosolvent is polysorbate 20 at a concentration of about 0.2%±0.03% w/v.

In one embodiment, the formulation comprises a thermal stabilizer at a concentration of from about 0.9%±0.135% w/v to about 10%±1.5% w/v. In one embodiment, the thermal stabilizer is a sugar. In one embodiment, the sugar is selected from the group consisting of sucrose, mannitol and trehalose. In a specific embodiment, the thermal stabilizer is sucrose at a concentration of about 5%±0.75% w/v.

In one embodiment, the formulation comprises a viscosity reducer at a concentration that is not more than about 100 mM. In one embodiment, the viscosity reducer is arginine. In a specific embodiment, the viscosity reducer is L-arginine hydrochloride at 25 mM±3.75 mM.

In a specific embodiment, the stable low viscosity isotonic liquid pharmaceutical formulation has a viscosity of about 8.5±2.5 cPoise and an osmolality of about 290±20 mOsm/kg, and comprises: (i) 150 mg/ml±15 mg/ml of an anti-hIL4-Rα antibody, wherein the antibody comprises an HCVR and an LCVR, each of which comprises an amino acid sequence of SEQ ID NO:1 and SEQ ID NO:5, respectively; (ii) 12.5 mM±1.9 mM acetate; (iii) 20 mM±3 mM histidine; (iv) 0.2%±0.03% w/v of polysorbate 20; (v) 5%±0.75% w/v of sucrose; and (vi) 25 mM±3.75 mM of L-arginine hydrochloride. According to this embodiment, (i) at least about 98% of the antibody retains its native conformation, as determined by size exclusion chromatography, when kept at 5° C. for at least about six months, (ii) at least about 90% of the antibody retains its native conformation, as determined by size exclusion chromatography, when kept at 45° C. for at least about eight weeks, (iii) less than about 45% of the antibody comprises an acidic form, as determined by cation exchange chromatography, when kept at 45° C. for about eight weeks, and (iv) less than about 4% of the antibody comprises an aggregated form, as determined by size exclusion chromatography, when kept at 25° C. for about six months.

In one aspect, a liquid pharmaceutical formulation of any of the preceding aspects is provided in a container. In one embodiment, the container is a glass vial. In another embodiment, the container is a microinfuser. In another embodiment, the container is a syringe. In one specific embodiment, the syringe comprises a fluorocarbon-coated plunger. In one specific embodiment, the syringe is a low tungsten syringe.

Other embodiments of the present invention will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference to describe in their entirety.

Pharmaceutical Formulations

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody, or an antigen-binding fragment thereof, which binds specifically to human interleukin-4 receptor alpha (hIL-4Rα). More specifically, the present invention includes pharmaceutical formulations that comprise: (i) a human antibody that specifically binds to hIL-4Rα; (ii) an acetate/histidine buffer system; (iii) an organic cosolvent that is a non-ionic surfactant; (iv) thermal stabilizer that is a carbohydrate; and (v) a viscosity reducer. Specific exemplary components and formulations included within the present invention are described in detail below.

Antibodies that Bind Specifically to hIL-4R

The pharmaceutical formulations of the present invention may comprise a human antibody, or an antigen-binding fragment thereof, that binds specifically to hIL-4Rα. As used herein, the term "hIL-4Rα" means a human cytokine receptor that specifically binds interleukin-4 (IL-4). In certain embodiments, the antibody contained within the pharmaceutical formulations of the present invention binds specifically to the extracellular domain of hIL-4Rα. An exemplary human IL-4 receptor alpha (hIL-4Rα) amino acid sequence is described in SEQ ID NO:25. Antibodies to hIL-4Rα are described in U.S. Pat. Nos. 7,605,237 and 7,608,693. The extracellular domain of hIL-4Rα is represented by the amino acid sequence of SEQ ID NO:26.

The term "antibody", as used herein, is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementary determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Unless specifically indicated otherwise, the term "antibody", as used herein, shall be understood to encompass complete antibody molecules as well as antigen-binding fragments thereof. The term "antigen-binding portion" or "antigen-binding fragment" of an antibody (or simply "antibody portion" or "antibody fragment"), as used herein, refers to one or more fragments of an antibody that retain the ability to specifically bind to hIL-4Rα or an epitope thereof.

An "isolated antibody", as used herein, is intended to refer to an antibody that is substantially free of other antibodies having different antigenic specificities (e.g., an isolated antibody that specifically binds hIL-4Rα is substantially free of antibodies that specifically bind antigens other than hIL-4Rα).

The term "specifically binds", or the like, means that an antibody or antigen-binding fragment thereof forms a complex with an antigen that is relatively stable under physiologic conditions. Specific binding can be characterized by a dissociation constant of at least about $1 \times 10^{-6}$ M or greater. Methods for determining whether two molecules specifically bind are well known in the art and include, for example, equilibrium dialysis, surface plasmon resonance, and the like. An isolated antibody that specifically binds hIL-4Rα may, however, have cross-reactivity to other antigens, such as IL-4R molecules from other species (orthologs). In the context of the present invention, multispecific (e.g., bispecific) antibodies that bind to hIL-4Rα as well as one or more additional antigens are deemed to "specifically bind" hIL-4Rα. Moreover, an isolated antibody may be substantially free of other cellular material or chemicals.

Exemplary anti-hIL-4Rα antibodies that may be included in the pharmaceutical formulations of the present invention are set forth in U.S. Pat. Nos. 7,605,237 and 7,608,693, the disclosures of which are incorporated by reference in their entirety.

According to certain embodiments of the present invention, the anti-hIL-4Rα antibody is a human IgG1 comprising a heavy chain variable region that is of the IGHV3-9 subtype and a light chain variable region that is of the IGKV2-28 subtype (see Barbie and Lefranc, The Human Immunoglobulin Kappa Variable (IGKV) Genes and Joining (IGKJ) Segments, Exp. Clin. Immunogenet. 1998; 15:171-183; and Scaviner, D. et al., Protein Displays of the Human Immunoglobulin Heavy, Kappa and Lambda Variable and Joining Regions, Exp. Clin. Immunogenet., 1999; 16:234-240).

In some embodiments, the anti-hIL-4Rα comprises at least one amino acid substitution, which results in a charge change at an exposed surface of the antibody relative to the germline IGHV3-9 sequence or the germline IGKV2-28 sequence. The germline IGHV3-9 and IGKV2-28 sequences, and the amino acid position assignment numbers presented herein comport with the international Immunogenetics (IMGT) information system, as described in Lefranc, M.-P., et al., IMGT®, the international ImMunoGeneTics information System®, Nucl. Acids Res, 37, D1006-D1012 (2009). In some embodiments, the exposed surface comprises a complementarity determining region (CDR). In some embodiments, the amino acid substitution or substitutions are selected from the group consisting of (a) a basic amino acid substituted for a neutral amino acid within CDR2 (e.g., at position 58) of IGHV3-9, (b) a neutral amino acid substituted for an acidic amino acid within CDR3 (e.g., at position 107) of IGHV3-9, and (c) a neutral amino acid substituted for a basic amino acid within CDR1 (e.g., at position 33) of IGKV2-28. Unique permutations in the charge distribution of an antibody, especially at an environmental interface (such as, e.g., in a CDR) would be expected to create unpredictable conditions for antibody stability in solution.

In some embodiments, the anti-hIL-4Rα antibody comprises at least one amino acid substitution, which creates a change in the torsional strain within a framework region of a variable region of the antibody relative to the germline IGHV3-9 sequence or the germline IGKV2-28 sequence. In some embodiments, the amino acid substitution or substitutions are selected from the group consisting of (a) a proline substituted for a non-proline amino acid in framework region 3 (FR3) (e.g., at position 96) of IGHV3-9, and (b) a non-proline amino acid substituted for a proline in framework region 2 (FR2) (e.g., at position 46) of IGKV2-28. Changes in the ability of the peptide chain to rotate, especially within a framework region, which affects the CDR interface with the solvent, would be expected to create unpredictable conditions for antibody stability in solution.

According to certain embodiments of the present invention, the anti-hIL-4Rα antibody, or antigen-binding fragment thereof, comprises a heavy chain complementary determining region (HCDR) 1 of SEQ ID NO: 2, an HCDR2 of SEQ ID NO:3, and an HCDR3 of SEQ ID NO: 4. In certain embodiments, the anti-hIL-4Rα antibody, or antigen-binding fragment thereof, comprises an HCVD of SEQ ID NO:1.

According to certain embodiments of the present invention, the anti-hIL-4Rα, or antigen-binding fragment thereof, comprises a light (kappa) chain complementary determining region (LCDR) 1 of SEQ ID NO: 6, an LCDR2 of SEQ ID NO: 7, and an LCDR3 of SEQ ID NO: 8. In certain embodiments, the anti-hIL-4Rα antibody, or antigen-binding fragment thereof, comprises an LCVD of SEQ ID NO:5.

According to certain other embodiments of the present invention, the anti-hIL-4Rα antibody, or antigen-binding fragment thereof, comprises an HCDR1 of SEQ ID NO: 10, an HCDR2 of SEQ ID NO:11, an HCDR3 of SEQ ID NO: 12, an LCDR1 of SEQ ID NO: 14, an LCDR2 of SEQ ID NO:15, and an LCDR3 of SEQ ID NO: 16. In certain embodiments, the anti-hIL-4Rα antibody, or antigen-binding fragment thereof, comprises an HCVD of SEQ ID NO:9 and an LCVD of SEQ ID NO:13.

According to certain other embodiments of the present invention, the anti-hIL-4Rα antibody, or antigen-binding fragment thereof, comprises an HCDR1 of SEQ ID NO: 18, an HCDR2 of SEQ ID NO:19, an HCDR3 of SEQ ID NO: 20, an LCDR1 of SEQ ID NO: 22, an LCDR2 of SEQ ID NO:23, and an LCDR3 of SEQ ID NO: 24. In certain embodiments, the anti-hIL-4Rα antibody, or antigen-binding fragment thereof, comprises an HCVD of SEQ ID NO:17 and an LCVD of SEQ ID NO:21.

The non-limiting, exemplary antibody used in the Examples herein is referred to as "mAb1". This antibody is also referred to in U.S. Pat. No. 7,608,693 as H4H098P. mAb1 (H4H098P) comprises an HCVR/LCVR amino acid sequence pair having SEQ ID NOs: 1/5, and HCDR1-HCDR2-HCDR3/LCDR1-LCDR2-LCDR3 domains represented by SEQ ID NOs: 2-3-4/SEQ ID NOS: 6-7-8.

Another non-limiting, exemplary antibody which may be used in the practice of this invention is referred to as "mAb2". This antibody is also referred to in U.S. Pat. No. 7,608,693 as H4H083P. mAb2 (H4H083P) comprises an HCVR/LCVR amino acid sequence pair having SEQ ID NOs: 9/13, and HCDR1-HCDR2-HCDR3/LCDR1-LCDR2-LCDR3 domains represented by SEQ ID NOs: 10-11-12/ SEQ ID NOs: 14-15-16.

Yet another non-limiting, exemplary antibody which may be used in the practice of this invention is referred to as "mAb3". This antibody is also referred to in U.S. Pat. No. 7,608,693 as H4H095P. mAb3 (H4H095P) comprises an HCVR/LCVR amino acid sequence pair having SEQ ID NOs: 17/21, and HCDR1-HCDR2-HCDR3/LCDR1-LCDR2-LCDR3 domains represented by SEQ ID NOs: 18-19-20/SEQ ID NOs: 22-23-24.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain about 100±10 mg/ml to about 200±20 mg/ml of antibody; about 110±11 mg/mL to about 190±19 mg/ml of antibody; about 120±12 mg/mL to about 180±18 mg/ml of antibody; about 130±13 mg/mL to about 170±17 mg/mL of antibody; about 140±14 mg/mL to about 160±16 mg/ml of antibody; or about 150±15 mg/mL of antibody. For example, the formulations of the present invention may comprise about 90 mg/ml; about 95 mg/mL; about 100 mg/mL; about 105 mg/ml; about 110 mg/ml; about 115 mg/mL; about 120 mg/mL; about 125 mg/mL; about 130 mg/mL; about 131 mg/ml; about 132 mg/mL; about 133 mg/mL; about 134 mg/mL; about 135 mg/mL; about 140 mg/mL; about 145 mg/mL; about 150 mg/mL; about 155 mg/mL; about 160 mg/ml; about 165 mg/mL; about 170 mg/mL; about 175 mg/mL; about 180 mg/mL; about 185 mg/mL; about 190 mg/mL; about 195 mg/mL; or about 200 mg/ml of an antibody or an antigen-binding fragment thereof, that binds specifically to hIL-4Rα.

Excipients and pH

The pharmaceutical formulations of the present invention comprise one or more excipients. The term "excipient", as used herein, means any non-therapeutic agent added to the formulation to provide a desired consistency, viscosity or stabilizing effect.

In certain embodiments, the pharmaceutical formulation of the invention comprises at least one organic cosolvent in a type and in an amount that stabilizes the hIL-4Rα antibody under conditions of rough handling, such as, e.g., vortexing. In some embodiments, what is meant by "stabilizes" is the prevention of the formation of more than 2% aggregated antibody of the total amount of antibody (on a molar basis) over the course of rough handling. In some embodiments, rough handling is vortexing a solution containing the antibody and the organic cosolvent for about 120 minutes.

In certain embodiments, the organic cosolvent is a nonionic surfactant, such as an alkyl poly(ethylene oxide). Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN 20, sorbitan monolaurate and polyoxyethylenesorbitan monolaurate. Poloxamer 181 is also known as PLURONIC F68.

The amount of organic cosolvent contained within the pharmaceutical formulations of the present invention may vary depending on the specific properties desired of the formulations, as well as the particular circumstances and purposes for which the formulations are intended to be used. In certain embodiments, the formulations may contain about 0.1%±0.01% to about 2%±0.2% surfactant. For example, the formulations of the present invention may comprise about 0.09%; about 0.10%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; or about 0.30% polysorbate 20 or poloxamer 181. For example, the formulations of the present invention may comprise about 0.5%; about 0.6%; about 0.7%; about 0.8%; about 0.9%; about 1%; about 1.1%; about 1.2%; about 1.3%; about 1.4%; about 1.5%; about 1.6%; about 1.7%; about 1.8%; about 1.9%; or about 2.0% PEG 3350.

Exemplary organic cosolvents that stabilize the hIL-4Rα antibody include 0.2%±0.02% polysorbate 20, 0.2%±0.02% poloxamer 181, or 1%±0.1% PEG 3350.

The pharmaceutical formulations of the present invention may also comprise one or more thermal stabilizers in a type and in an amount that stabilizes the hIL-4Rα antibody under conditions of thermal stress. In some embodiments, what is meant by "stabilizes" is maintaining greater than about 92% of the antibody in a native conformation when the solution containing the antibody and the thermal stabilizer is kept at about 45° C. for up to about 28 days. In some embodiments, what is meant by "stabilizes" is wherein less than about 5% of the antibody is aggregated when the solution containing the antibody and the thermal stabilizer is kept at about 45° C. for up to about 28 days.

In certain embodiments, the thermal stabilizer is a sugar or sugar alcohol selected from sucrose, trehalose and mannitol, or any combination thereof, the amount of which contained within the formulation can vary depending on the specific circumstances and intended purposes for which the formulation is used. In certain embodiments, the formulations may contain about 2.5% to about 10% sugar or sugar alcohol; about 3% to about 9.5% sugar or sugar alcohol; about 3.5% to about 9% sugar or sugar alcohol; about 4% to about 8.5% sugar or sugar alcohol; about 4.5% to about 8% sugar or sugar alcohol; about 5% to about 7.5% sugar or sugar alcohol; about 5.5% to about 7% sugar or sugar alcohol; or about 6.0% to about 6.5% sugar or sugar alcohol. For example, the pharmaceutical formulations of the present invention may comprise about 2.5%±0.375%; about 3%±0.45%; about 3.5%±0.525%; about 4.0%±0.6%; about 4.5%±0.675%; about 5.0%±0.75%; about 5.5%±0.825%; about 6.0%±0.9%; about 6.5%±0.975%; about 7.0%±1.05%; about 7.5%±1.125%; about 8.0%±1.2%; 8.5%±1.275%; about 9.0%±1.35%; or about 10.0%±1.5% sugar or sugar alcohol (e.g., sucrose, trehalose or mannitol).

The pharmaceutical formulations of the present invention may also comprise a buffer or buffer system, which serves to maintain a stable pH and to help stabilize the hIL-4Rα antibody. In some embodiments, what is meant by "stabilizes" is wherein less than 3.0%±0.5% of the antibody is aggregated when the solution containing the antibody and the buffer is kept at about 45° C. for up to about 14 days. In some embodiments, what is meant by "stabilizes" is wherein less than 3.7%±0.5% of the antibody is aggregated when the solution containing the antibody and the buffer is kept at about 25° C. for up to about 6 months. In some embodiments, what is meant by "stabilizes" is wherein at least 95%±0.5% of the antibody is in its native conformation as determined by size exclusion chromatography when the solution containing the antibody and the buffer is kept at about 45° C. for up to about 14 days. In some embodiments, what is meant by "stabilizes" is wherein at least 96%±0.5% of the antibody is in its native conformation as determined by size exclusion chromatography when the solution containing the antibody and the buffer is kept at about 25° C. for up to about 6 months. In some embodiments, what is meant by "stabilizes" is wherein at least 62%±0.5% of the antibody is in its neutral conformation as determined by cation exchange chromatography when the solution containing the antibody and the buffer is kept at about 45° C. for up to about 14 days. In some embodiments, what is meant by "stabilizes" is wherein at least 54%±0.5% of the antibody is in its neutral conformation as determined by cation exchange chromatography when the solution containing the antibody and the buffer is kept at about 25° C. for up to about 6 months. By "neutral conformation", what is meant is the faction of antibody that elutes from an ion exchange resin in the main peak, which is generally flanked by more "basic" peaks on one side and more "acidic" peaks on the other side.

The pharmaceutical formulations of the present invention may have a pH of from about 5.2 to about 6.4. For example, the formulations of the present invention may have a pH of about 5.2; about 5.3; about 5.4; about 5.5; about 5.6; about 5.7; about 5.8; about 5.9; about 6.0; about 6.1; about 6.2; about 6.3; or about 6.4. In some embodiments, the pH is about 5.3±0.2; about 5.9±0.2; or about 6.0±0.2.

In some embodiments, the buffer or buffer system comprises at least one buffer that has a buffering range that overlaps fully or in part the range of pH 5.2-6.4. In one embodiment, the buffer or buffer system comprises two buffers, the first of which has an effective pH range within 3.6-5.6 and the second of which has an effective pH range within 5.5-7.4. In one embodiment, the first buffer has a pKa of about 4.8±0.3 and the second buffer has a pKa of about 6.0±0.3. In certain embodiments, the buffer system comprises an acetate buffer and a histidine buffer. In certain embodiments, the histidine is present at about 1.3-1.9 parts per 1 part of acetate by mole. In certain embodiments, the histidine is present at about 1.6±0.25 parts to 1 part of acetate by mole. In certain embodiments, the acetate is present at a concentration of about 2.5 mM to about 22.5 mM; about 3.0 mM to about 22 mM; about 3.5 mM to about 21.5 mM; about 4.0 mM to about 21.0 mM; about 4.5 mM to about 20.5 mM; about 5.0 mM to about 20 mM; about 5.5 mM to about 19.5 mM; about 6.0 mM to about 19.0 mM; about 6.5 mM to about 18.5 mM; about 7.0 mM to about 18.0 mM; about 7.5 mM to about 17.5 mM; about 8.0 mM to about 17 mM; about 8.5 mM to about 16.5 mM; about 9.0 mM to about 16.0 mM; about 9.5 mM to about 15.5 mM; about 10.0 mM to about 15.0 mM; about 10.5 mM to about 14.5 mM; about 12.5 mM±1.875 mM; about 11.0 mM to about 14.0 mM; about 11.5 mM to about 13.5 mM; or about 12.0 mM to about 13.0 mM. In certain embodiments, the histidine is present at a concentration of about 10 mM to about 30 mM; about 11 mM to about 29 mM; about 12 mM to about 28 mM; about 13 mM to about 27 mM; about 14 mM to about 26 mM; about 15 mM to about 25 mM; about 16 mM to about 24 mM; about 17 mM to about 23 mM; about 18 mM to about 22 mM; or about 19 mM to about 21 mM. In certain embodiments, the buffer system comprises acetate at about 12.5 mM and histidine at about 20 mM, at a pH of about 5.9.

The pharmaceutical formulations of the present invention may also comprise one or more excipients, which serve to maintain a reduced viscosity or to lower the viscosity of formulations containing a high concentration of protein (e.g., generally >100 mg/ml of protein). In some embodiments, the formulation comprises arginine in an amount sufficient to maintain the viscosity of the liquid formulation at less than about 35 cPoise, less than about 30 cPoise, less than about 25 cPoise, less than about 20 cPoise, less than about 15 cPoise, less than about 14 cPoise, less than about 13 cPoise, less than about 12 cPoise, less than about 10 cPoise, or less than about 9 cPoise.

In certain embodiments, the pharmaceutical formulation of the present invention contains arginine, preferably as L-arginine hydrochloride, at a concentration of about 25 mM±3.75 mM, about 50 mM±7.5 mM, or about 100 mM±15 mM. In certain embodiments, the arginine is at about 20 mM to about 30 mM, about 21 mM to about 29 mM, about 21.25 mM to about 28.75 mM, about 22 mM to about 28 mM, about 23 mM to about 27 mM or about 24 mM to about 26 mM.

Exemplary Formulations

According to one aspect of the present invention, the pharmaceutical formulation is a low viscosity, generally physiologically isotonic liquid formulation, which comprises: (i) a human antibody that specifically binds to hIL-4Rα (e.g., mAb1, mAb2 or mAb3 [supra]), at a concentration of about 100 mg/ml or greater; (ii) a buffer system that provides sufficient buffering at about 5.9±0.6; (iii) a sugar which serves inter alia as a thermal stabilizer; (iv) an organic cosolvent, which protects the structural integrity if the antibody; and (v) an amino acid, which serves to keep the viscosity manageable for subcutaneous injection.

According to one embodiment, the pharmaceutical formulation comprises: (i) a human IgG1 antibody that specifically binds to hIL-4Rα and which comprises a substituted IGHV3-9 type heavy chain variable region and a substituted IGLV2-28 type light chain variable region (e.g., mAb1) at a concentration from about 100 mg/ml to about 200 mg/ml; (ii) a buffer system comprising acetate and histidine, which buffers effectively at about pH 5.9±0.6; (iii) sucrose as a thermal stabilizer; (iv) a polysorbate as an organic cosolvent; and (v) arginine as a viscosity reducer.

According to one embodiment, the pharmaceutical formulation comprises: (i) a human IgG1 antibody that specifically binds to hIL-4Rα, and which comprises an HCDR1 of SEQ ID NO: 2, an HCDR2 of SEQ ID NO:3, an HCDR3 of SEQ ID NO:4, an LCDR1 of SEQ ID NO:6, an LCDR2 of SEQ ID NO:7, and an LCDR3 of SEQ ID NO:8, at a concentration of about 150 mg/ml±25 mg/ml; (ii) acetate at about 12.5 mM±1.9 mM and histidine at about 20 mM±3 mM, which buffers effectively at about pH 5.9±0.3; (iii) sucrose at about 5% w/v±0.75% w/v; (iv) polysorbate 20 at about 0.2% w/v±0.03% w/v; and (v) arginine as L-arginine hydrochloride at about 25 mM±3.75 mM.

Additional non-limiting examples of pharmaceutical formulations encompassed by the present invention are set forth elsewhere herein, including the working Examples presented below.

Stability and Viscosity of the Pharmaceutical Formulations

The pharmaceutical formulations of the present invention typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of about 90%, about 95%, about 96%, about 97%, about 98% or about 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion high performance liquid chromatography [SE-HPLC]). An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 2 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 45° C., e.g., storage at about −30° C., about −20° C., about 0° C., about 4°-8° C., about 5° C., about 25° C., or about 45° C. For example, a pharmaceutical formulation may be deemed stable if after 3 months of storage at 5° C., greater than about 90%, 95%, 96%, 97% or 98% of native antibody is detected by SE-HPLC. A pharmaceutical formulation may also be deemed stable if after 6 months of storage at 5° C., greater than about 90%, 95%, 96%, 97% or 98% of native antibody is detected by SE-HPLC. A pharmaceutical formulation may also be deemed stable if after 9 months of storage at 5° C., greater than about 90%, 95%, 96%, 97% or 98% of native antibody is detected by SE-HPLC. A pharmaceutical formulation may also be deemed stable if after 3 months of storage at 25° C., greater than about 90%, 95%, 96% or 97% of native antibody is detected by SE-HPLC. A pharmaceutical formulation may also be deemed stable if after 6 months of storage at 25° C., greater than about 90%, 95%, 96% or 97% of native antibody is detected by SE-HPLC. A pharmaceutical formulation may also be deemed stable if after 9 months of storage at 25° C., greater than about 90%, 95%, 96% or 97% of native antibody is detected by SE-HPLC.

Stability can be measured, inter alia, by determining the percentage of antibody that forms in an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion high performance liquid chromatography [SE-HPLC]). An "acceptable degree of stability", as that phrase is used herein, means that at most 5% of the antibody is in an aggregated form detected in the formulation after storage for a defined amount of time at a given temperature. In certain embodiments an acceptable degree of stability means that at most about 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −30° C., about −20° C., about 0° C., about 4°-8° C., about 5° C., about 25° C., or about 45° C. For example, a pharmaceutical formulation may be deemed stable if after 3 months of storage at 5° C., less than about 5%, 4%, 3%, 2%, 1%, 0.5%, or 0.1% of the antibody is detected in an aggregated form. A pharmaceutical formulation may also be deemed stable if after 6 months of storage at 5° C., less than about 5%, 4%, 3%, 2%, 1%, 0.5%, or 0.1% of the antibody is detected in an aggregated form. A pharmaceutical formulation may also be deemed stable if after 9 months of storage at 5° C., less than about 5%, 4%, 3%, 2%, 1%, 0.5%, or 0.1% of the antibody is detected in an aggregated form. A pharmaceutical formulation may also be deemed stable if after 3 months of storage at 25° C., less than about 5%, 4%, 3%, 2%, 1%, 0.5%, or 0.1% of the antibody is detected in an aggregated form. A pharmaceutical formulation may also be deemed stable if after 6 months of storage at 25° C., less than about 5%, 4%, 3%, 2%, 1%, 0.5%, or 0.1% of the antibody is detected in an aggregated form. A pharmaceutical formulation may also be deemed stable if after 9 months of storage at 25° C., less than about 5%, 4%, 3%, 2%, 1%, 0.5%, or 0.1% of the antibody is detected in an aggregated form.

Stability can be measured, inter alia, by determining the percentage of antibody that migrates in a more acidic fraction during ion exchange ("acidic form") than in the main fraction of antibody ("neutral conformation"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, *PNAS*, Apr. 16, 2002, 99(8):5283-5288). The percentage of "acidified" or "deamidated" antibody can be determined by, inter alia, ion exchange chromatography (e.g., cation exchange high performance liquid chromatography [CEX-HPLC]). An "acceptable degree of stability", as that phrase is used herein, means that at most 45% of the antibody is in a more acidic form detected in the formulation after storage for a defined amount of time at a defined temperature. In certain embodiments an acceptable degree of stability means that at most about 45%, 40%, 35%, 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −30° C., about −20° C., about 0° C., about 4°-8° C., about 5° C., about 25° C., or about 45° C. For example, a pharmaceutical formulation may be deemed stable if after 3 months of storage at 5° C., less than about 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 3 months of storage at 25° C., less than about 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 8 weeks of storage at 45° C., less than about 45%, 40%, 35%, 30%, 25%, 20%, 15%, 10%, 5%, 4%, 3%, 2%, 1%, 0.5%, or 0.1% of the antibody is in a more acidic form. A pharmaceutical formulation may also be deemed stable if after 2 weeks of storage at 40° C., less than about 20%, 19%, 18%, 17%, 16%, 15%, 14%, 13%, 12%, 11%, 10%, 9%, 8%, 7%, 6%, 5%, 4%, 3%, 2%, 1%, 0.5%, or 0.1% of the antibody can be detected in a more acidic form.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

Stability may also be assessed by measuring the biological activity or binding affinity of the antibody to its target. For example, a formulation of the present invention may be regarded as stable if, after storage at e.g., 5° C., 25° C., 45° C., etc. for a defined amount of time (e.g., 1 to 12 months), the anti-IL-4Rα antibody contained within the formulation binds to IL-4Rα with an affinity that is at least 90%, 95%, or more of the binding affinity of the antibody prior to said storage. Binding affinity may be determined by e.g., ELISA or plasmon resonance. Biological activity may be determined by an IL-4Rα activity assay, such as e.g., contacting a cell that expresses IL-4Rα with the formulation comprising the anti IL-4Rα antibody. The binding of the antibody to such a cell may be measured directly, such as e.g., via FACS analysis. Alternatively, the downstream activity of the IL-4Rα system may be measured in the presence of the antibody and an IL-4Rα agonist, and compared to the activity of the IL-4Rα system in the absence of antibody. In some embodiments, the IL-4Rα may be endogenous to the cell. In other embodiments, the IL-4Rα may be ectopically expressed in the cell.

Additional methods for assessing the stability of an antibody in formulation are demonstrated in the Examples presented below.

The liquid pharmaceutical formulations of the present invention may, in certain embodiments, exhibit low to moderate levels of viscosity. "Viscosity" as used herein may be "kinematic viscosity" or "absolute viscosity". "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, a low level of viscosity, in reference to a fluid formulation of the present invention, will exhibit an absolute viscosity of less than about 15 cPoise (cP). For example, a fluid formulation of the invention will be deemed to have "low viscosity", if, when measured using standard viscosity measurement techniques, the formulation exhibits an absolute viscosity of about 15 cP, about 14 cP, about 13 cP, about 12 cP, about 11 cP, about 10 cP, about 9 cP, about 8 cP, or less. As used herein, a moderate level of viscosity, in reference to a fluid formulation of the present invention, will exhibit an absolute viscosity of between about 35 cP and about 15 cP. For example, a fluid formulation of the invention will be deemed to have "moderate viscosity", if when measured using standard viscosity measurement techniques, the formulation exhibits an absolute viscosity of about 34 cP, about 33 cP, about 32 cP, about 31 cP, about 30 cP, about 29 cP, about 28 cP, about 27 cP, about 26 cP, about 25 cP, about 24 cP, about 23 cP, about 22 cP, about 21 cP, about 20 cP, about 19 cP, 18 cP, about 17 cP, about 16 cP, or about 15.1 cP.

As illustrated in the examples below, the present inventors have made the surprising discovery that low to moderate viscosity liquid formulations comprising high concentrations of an anti-hIL-4Rα antibody (e.g., from about 100 mg/ml up to at least 200 mg/mL) can be obtained by formulating the antibody with arginine from about 25 mM to about 100 mM. In addition, it was further discovered that the viscosity of the formulation could be decreased to an even greater extent by adjusting the sucrose content to less than about 10%.

Containers for the Pharmaceutical Formulations and Methods of Administration

The pharmaceutical formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present invention including, e.g., clear and opaque (e.g., amber) glass or plastic vials. Likewise, any type of syringe can be used to contain or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®", available from West Pharmaceutical Services, Inc. (Lionville, PA).

According to certain embodiments of the present invention, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMA-LOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present invention include, but are not limited to the SOLOSTART pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park, IL).

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In one embodiment, the liquid pharmaceutical formulation containing about 150 mg/ml±15 mg/ml anti-IL-4Rα antibody is administered subcutaneously in a volume of approximately 1 ml±0.15 ml from a prefilled syringe in an autoinjector. In another embodiment, the formulation is administered in a volume of between about 1 ml and 2.5 ml from a microinfuser device. The formulation may be prefilled in a pouch or a cartridge for use in the microinfuser.

Therapeutic Uses of the Pharmaceutical Formulations

The pharmaceutical formulations of the present invention are useful, inter alia, for the treatment, prevention or amelioration of any disease or disorder associated with IL-4 activity, including diseases or disorders mediated by activation of IL-4Rα. Exemplary, non-limiting diseases and disorders that can be treated or prevented by the administration of the pharmaceutical formulations of the present invention include various atopic diseases such as, e.g., atopic dermatitis, allergic conjunctivitis, allergic rhinitis, asthma and other IgE/Th2 mediated diseases.

Thus, the present invention includes methods of treating, preventing, or ameliorating any disease or disorder associated with IL-4 activity or IL-4Rα activation (including any of the above mentioned exemplary diseases, disorders and conditions). The therapeutic methods of the present invention comprise administering to a subject any formulation comprising an anti-hIL-4Rα antibody as disclosed herein. The subject to which the pharmaceutical formulation is administered can be, e.g., any human or non-human animal that is in need of such treatment, prevention or amelioration, or who would otherwise benefit from the inhibition or attenuation of IL-4 or IL-4Rα-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention or amelioration of any disease or disorder associated with IL-4 activity or IL-4Rα activation (including any of the above mentioned exemplary diseases, disorders and conditions).

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, temperature is in degrees Centigrade, and pressure is at or near atmospheric pressure.

Initial formulation development activities involved screening organic cosolvents, thermal stabilizers, and buffers in liquid formulations of mAb1 (anti-IL-4Rα antibody of the invention) to identify excipients that are compatible with the protein and enhance its stability, while maintaining osmolality and viscosity for subcutaneous injection. Buffer conditions were also examined to determine the optimal pH for maximum protein stability.

observed to decrease the thermal stability of mAb1 (Table 2). A loss of protein recovery was observed in formulations containing PEG 3350 (3%) and PEG 300 (10% and 20%) as determined by RP-HPLC following thermal stress (Table 2). In addition, there was more aggregate formation in the formulations containing PLURONIC F68 (poloxamer 181) (0.2%), PEG 300 (10% and 20%), and Propylene Glycol (20%) than in the formulation without cosolvent as determined by SE-HPLC. Polysorbate 20 (0.2%) and polysorbate 80 (0.2%) provided comparable stability to agitation and thermal stress.

According to Table 1, 0.3 ml of 15 mg/ml of mAb1 in 10 mM phosphate, pH 6.0, and various organic cosolvents in a 2 ml glass vial were subjected to vortexing for about 120 minutes. Turbidity was assessed via optical density (OD) at 405 nm and reported as the relative change in OD at 405 nm as compared to the starting material. The percent of total mAb1 recovered was determined via reverse phase HPLC (RP-HPLC). The percent native and aggregated mAb1 was determined via size exclusion HPLC (SE-HPLC). The SE-HPLC results presented in the "Starting Material" results are the average of the values of each of the formulations in the absence of vortexing.

TABLE 1

| Organic Cosolvent | Visual Appearance | Turbidity | pH | % Total mAb1 (RP-HPLC) | % Native mAb1 (SE-HPLC) | % mAb1 Aggregate (SE-HPLC) |
|---|---|---|---|---|---|---|
| Starting Material[2] (no vortexing) | Pass | 0.00 | 6.0 | 100 | 96.8 | 1.8 |
| No Cosolvent | Fail | 0.87 | 6.0 | 86 | 95.6 | 3.5 |
| 0.2% Polysorbate 20 | Pass | 0.01 | 5.9 | 98 | 97.0 | 1.7 |
| 0.2% Polysorbate 80 | Pass | 0.00 | 5.9 | 100 | 96.6 | 2.0 |
| 0.2% Pluronic F68 | Pass | 0.00 | 5.9 | 99 | 96.9 | 1.7 |
| 3% PEG 3350 | Pass | 0.00 | 6.0 | 102 | 96.7 | 2.0 |
| 1% PEG 3350 | Pass | 0.01 | 6.0 | 99 | 96.8 | 1.8 |
| 20% PEG 300 | Pass | 0.01 | 5.9 | 101 | 96.1 | 2.6 |
| 10% PEG 300 | Pass | 0.01 | 6.0 | 100 | 96.7 | 2.0 |
| 20% Propylene Glycol | Pass | 0.00 | 6.0 | 101 | 96.7 | 2.0 |

Example 1. Organic Cosolvents

It was observed that mAb1 is unstable when subjected to agitation stress. Analysis by reverse phase high performance liquid chromatography (RP-HPLC) and size exclusion high performance liquid chromatography (SE-HPLC) demonstrated a loss of protein and an increase of protein aggregates when mAb1 was vortexed at room temperature (Table 1, see "No Cosolvent" data). The addition of organic cosolvents to the mAb1 solution prevented the protein from degradation, as measured by SE-HPLC and RP-HPLC (Table 1). However, the additions of some of the organic cosolvents were According to Table 2, 0.3 ml of 15 mg/ml of mAb1 in 10 mM phosphate, pH 6.0, and various organic cosolvents in a 2 ml glass vial were kept at about 45° C. for about 28 days. Turbidity was assessed via optical density (OD) at 405 nm and reported as the relative change in OD at 405 nm as compared to the starting material. The percent of total mAb1 recovered was determined via reverse phase HPLC (RP-HPLC). The percent native and aggregated mAb1 was determined via size exclusion HPLC (SE-HPLC). The SE-HPLC results presented in the "Starting Material" results are the average of the values of each of the formulations in the absence of thermal stress.

TABLE 2

| Organic Cosolvent | Visual Appearance | Turbidity | pH | % Total mAb1 (RP-HPLC) | % Native mAb1 (SE-HPLC) | % mAb1 Aggregate (SE-HPLC) |
|---|---|---|---|---|---|---|
| Starting Material (no acceleration) | Pass | 0.00 | 6.0 | 100 | 96.8 | 1.8 |
| No Cosolvent | Pass | 0.00 | 6.2 | 98 | 94.9 | 3.5 |
| 0.2% Polysorbate 20 | Pass | 0.00 | 6.3 | 98 | 94.6 | 3.6 |
| 0.2% Polysorbate 80 | Pass | 0.00 | 6.2 | 97 | 94.3 | 3.8 |
| 0.2% Pluronic F68 | Pass | 0.00 | 6.2 | 96 | 93.0 | 5.1 |

TABLE 2-continued

| Organic Cosolvent | Visual Appearance | Turbidity | pH | % Total mAb1 (RP-HPLC) | % Native mAb1 (SE-HPLC) | % mAb1 Aggregate (SE-HPLC) |
|---|---|---|---|---|---|---|
| 3% PEG 3350 | Pass | 0.00 | 6.2 | 73 | 96.5 | 1.4 |
| 1% PEG 3350 | Pass | 0.01 | 6.0 | 97 | 94.6 | 3.8 |
| 20% PEG 300 | Pass | 0.04 | 4.5 | 74 | 8.5 | 87.5 |
| 10% PEG 300 | Pass | 0.02 | 4.8 | 93 | 57.7 | 38.1 |
| 20% Propylene Glycol | Pass | 0.00 | 6.3 | 97 | 93.6 | 4.7 |

Example 2. Thermal Stabilizers

Various thermal stabilizers, such as sugars, amino acids, and inorganic salts, were examined for their ability to inhibit the degradation of mAb1 when kept at about 45° C. A summary of the thermal stabilizers studied is presented in Table 3. Formulations containing either sucrose or trehalose had the greatest stabilizing effect for mAb1 in solution when incubated at elevated temperature (as determined by SE-HPLC). Sucrose was selected as the stabilizer since it has a safe history of use in monoclonal antibody formulations.

According to Table 3, 0.3 ml of 25 mg/ml of mAb1 in 10 mM acetate, pH 5.3, and various thermal stabilizers in a 2 ml glass vial were kept at about 45° C. for about 28 days. Turbidity was assessed via optical density (OD) at 405 nm and reported as the relative change in OD at 405 nm as compared to the starting material. Turbidity was negligible for all samples. The percent of total mAb1 recovered was determined via reverse phase HPLC (RP-HPLC). The percent native and aggregated mAb1 was determined via size exclusion HPLC (SE-HPLC). Acidic or basic species are defined as the sum of the mAb1 peaks that elute from the cation exchange (CEX-HPLC) column with earlier or later retention times than the main peak, respectively. The SE-HPLC results presented in the "Starting Material" results are the average of the values of each of the formulations in the absence of thermal stress.

Example 3. Buffers and pH

The effect of pH and buffer species on mAb1 stability was also examined. 15 mg/mL of mAb1 was incubated in different buffers at different pH values ranging from pH 4.5 to 7.0. Protein stability was monitored by SE-HPLC and cation exchange HPLC (CEX-HPLC). Maximum protein stability was observed, as determined by both SE-HPLC and CEX-HPLC, when mAb1 was formulated at pH 6.0 in histidine buffer or at pH 5.3 in acetate buffer (Table 4 and Table 5). The acetate buffer system provided a broader pH stability range and lower rate of charge variant formation relative to the formulation containing histidine buffer (Table 5). Therefore, acetate buffer, at pH 5.3, was selected in part for the formulation of the mAb1 drug substance.

According to Table 4, 0.3 ml of 15 mg/ml of mAb1, 0.2% polysorbate 20, combined with 10 mM of various buffers in a 2 ml glass vial were kept at about 45° C. for about 14 days. Turbidity was assessed via optical density (OD) at 405 nm and reported as the relative change in OD at 405 nm as compared to the starting material. Turbidity was negligible for all samples. The percent of total mAb1 recovered was determined via reverse phase HPLC (RP-HPLC). The percent native and aggregated mAb1 was determined via size exclusion HPLC (SE-HPLC). Acidic or basic species are defined as the sum of the mAb1 peaks that elute from the cation exchange (CEX-HPLC) column with earlier or later retention times than the main peak, respectively. The SE-HPLC results presented in the "Starting Material" results are the average of the values of each of the formulations in the absence of thermal stress.

TABLE 3

| Buffer and pH | pH | % Total mAb1 (RP-HPLC) | % Native mAb1 (SE-HPLC) | % mAb1 Aggregate (SE-HPLC) | % mAb1 (CEX- HPLC) Acidic Peak | Main Peak | Basic Peak |
|---|---|---|---|---|---|---|---|
| Starting Material (no 45° C. incubation) | 5.3 | 100 | 97.8 | 1.2 | 17.6 | 68.2 | 13.2 |
| No Thermal Stabilizer | 5.4 | 106 | 91.9 | 5.8 | 28.1 | 56.5 | 15.4 |
| 8.5% Sucrose | 5.4 | 105 | 93.3 | 4.6 | 29.5 | 54.7 | 15.8 |
| 4.5% Sorbitol | 5.3 | 105 | 91.2 | 6.6 | 34.4 | 51.5 | 14.1 |
| 4.5% Mannitol | 5.3 | 104 | 92.6 | 5.2 | 28.4 | 56.0 | 15.6 |
| 9.4% Trehalose dihydrate | 5.4 | 103 | 93.4 | 4.5 | 29.1 | 55.6 | 15.3 |
| 2.2% Glycine | 5.4 | 104 | 86.6 | 10.6 | 33.5 | 50.7 | 15.8 |
| 0.9% NaCl | 5.4 | 98 | 85.0 | 8.7 | 25.2 | 56.0 | 18.7 |
| 2.5% Glycerol | 5.4 | 104 | 91.9 | 6.0 | 29.7 | 56.1 | 14.3 |
| 5% Arginine | 5.4 | 97 | 83.2 | 11.4 | 25.3 | 57.1 | 17.6 |

TABLE 4

| Buffer and pH | % Total mAb1 Recovered (RP-HPLC) | % Native mAb1 Recovered (SE-HPLC) | % mAb1 Aggregate Recovered (SE-HPLC) | % mAb1 Recovered[2] (CEX-HPLC) | | |
|---|---|---|---|---|---|---|
| | | | | Acidic Peaks | Main Peak | Basic Peaks |
| Starting Material[3] (no 45° C. incubation) | 100 | 96.8 | 1.7 | 19.1 | 66.4 | 14.5 |
| pH 7.0, Phosphate | 97 | 93.9 | 4.5 | 39.1 | 50.1 | 10.8 |
| pH 6.5, Phosphate | 96 | 94.4 | 4.0 | 31.7 | 55.9 | 12.5 |
| pH 6.0, Phosphate | 99 | 95.2 | 3.1 | 23.8 | 62.2 | 14.0 |
| pH 6.0, Histidine | 97 | 95.5 | 2.8 | 23.9 | 61.8 | 14.3 |
| pH 6.0, Succinate | 99 | 94.8 | 3.5 | 26.7 | 59.6 | 13.7 |
| pH 6.0, Citrate | 98 | 95.5 | 2.9 | 26.1 | 59.8 | 14.1 |
| pH 5.5, Citrate | 96 | 94.7 | 3.4 | 25.0 | 60.9 | 14.2 |
| pH 5.0, Citrate | 97 | 89.5 | 7.4 | 23.6 | 61.5 | 15.0 |
| pH 5.0, Acetate | 94 | 94.7 | 3.6 | 18.1 | 66.3 | 15.5 |
| pH 4.5, Acetate | 94 | 89.9 | 8.3 | 20.8 | 62.8 | 16.4 |

According to Table 5, 0.3 ml of 15 mg/ml of mAb1, 0.2% polysorbate 20, combined with 10 mM of various buffers in a 2 ml glass vial were stored at about 45° C. for about 14 days. Turbidity was assessed via optical density (OD) at 405 nm and reported as the relative change in OD at 405 nm as compared to the starting material. Turbidity was negligible for all samples. The percent of total mAb1 recovered was determined via reverse phase HPLC (RP-HPLC). The percent native and aggregated mAb1 was determined via size exclusion HPLC (SE-HPLC). Acidic or basic species are defined as the sum of the mAb1 peaks that elute from the cation exchange (CEX-HPLC) column with earlier or later retention times than the main peak, respectively. The SE-HPLC results presented in the "Starting Material" results are the average of the values of each of the formulations in the absence of thermal stress.

Formulation development studies indicated that under basic conditions (pH≥6.5), mAb1 in solution may deamidate. Conversely, below pH 5.0, the rate of formation of molecular weight variants of mAb1 was observed to increase. Based on these data, the pH of the mAb1 formulation was maintained between pH 5.6 and pH 6.2. mAb1 was observed to be stable over this pH range.

The effect of pH and buffer species on the stability of mAb1 was further evaluated in formulations containing either 20 mM histidine pH 6, 12.5 mM acetate pH 5.3, or a combination of 20 mM histidine and 12.5 acetate pH 5.9 (Table 6). Compared to the individual buffer system, mAb1 was most stable in a formulation containing both histidine and acetate at approximately pH 5.9. The slowest rate of aggregation was detected when mAb1 was formulated in this combined buffer system (SE-HPLC) (Table 6).

According to Table 6, 0.4 ml of 150 mg/ml of mAb1, 10% sucrose, 0.2% polysorbate 20, combined with various buffers in a 2 ml glass vial were kept at about 45° C. for about 14 days. Turbidity was assessed via optical density (OD) at 405 nm and reported as the relative change in OD at 405 nm as compared to the starting material. Turbidity was negligible for all samples. The percent of total mAb1 recovered was determined via reverse phase HPLC (RP-HPLC). The percent native and aggregated mAb1 was determined via size exclusion HPLC (SE-HPLC). Acidic or basic species are defined as the sum of the mAb1 peaks that elute from the cation exchange (CEX-HPLC) column with earlier or later retention times than the main peak, respectively. The SE-HPLC results presented in the "Starting Material" results are the average of the values of each of the formulations in the absence of thermal stress.

TABLE 5

| Buffer and pH | % Total mAb1 Recovered (RP-HPLC) | % Native mAb1 Recovered (SE-HPLC) | % mAb1 Aggregate Recovered (SE-HPLC) | % Native mAb1 Recovered (CEX-HPLC) | | |
|---|---|---|---|---|---|---|
| | | | | Acidic Peaks | Main Peak | Basic Peaks |
| Starting Material[3] (no 45° C. incubation) | 100 | 96.5 | 2.1 | 18.7 | 66.7 | 14.6 |
| pH 5.5, Histidine | 94 | 87.5 | 9.1 | 22.7 | 58.7 | 18.6 |
| pH 6.0, Histidine | 100 | 96.6 | 2.4 | 22.7 | 63.0 | 14.2 |
| pH 6.5, Histidine | 97 | 89.8 | 7.7 | 32.1 | 43.8 | 24.0 |
| pH 4.7, Acetate | 90 | 90.1 | 6.4 | 18.4 | 66.1 | 15.5 |
| pH 5.0, Acetate | 100 | 93.7 | 4.3 | 18.0 | 67.0 | 15.0 |
| pH 5.3, Acetate | 99 | 95.2 | 3.0 | 18.1 | 67.5 | 14.5 |
| pH 5.6, Acetate | 100 | 93.6 | 5.3 | 22.1 | 61.7 | 14.3 |

Table 6

TABLE 6

| Buffer and pH | % Total mAb1 Recovered (RP-HPLC) | % Native mAb1 Recovered (SE-HPLC) | % mAb1 Aggregate Recovered (SE-HPLC) | % mAb1 Recovered[2] (CEX-HPLC) | | |
|---|---|---|---|---|---|---|
| | | | | Acidic Peaks | Main Peak | Basic Peaks |
| Starting Material[3] (no 45° C. incubation) | 100 | 97.0 | 2.6 | 27.4 | 62.1 | 10.5 |
| 20 mM Histidine, pH 5.9 | 100 | 95.2 | 4.3 | 34.8 | 53.9 | 11.4 |
| 12.5 mM Acetate, pH 5.3, | 103 | 94.8 | 4.8 | 30.9 | 56.0 | 13.1 |
| Combined 20 mM Histidine & 12.5 mM Acetate, pH 5.9 | 104 | 95.9 | 3.7 | 33.7 | 54.1 | 12.1 |

Example 4. Management of Viscosity and Tonicity

Combinations of various excipients with high concentrations of mAb1 (i.e., 150 mg/ml, 175 mg/ml and 200 mg/ml) were assessed for viscosity and tonicity (as expressed in osmolality). The levels of sucrose, sodium chloride and L-arginine hydrochloride were adjusted to develop a formulation containing a high concentration of mAb1 at a low viscosity and at a physiological tonicity to enable the easy, comfortable and fast subcutaneous delivery of a high amount of mAb1 (Table 7). The liquid formulation containing 25 mM arginine, 20 mM histidine, 12.5 mM acetate, 5%

In addition, no affect on solution pH, turbidity, or on the amount of recovered mAb1 was observed. Following incubation of formulated mAb1 for 3 months at 25° C., the antibody was not significantly degraded as determined by SE-HPLC and there was 3.3% more degraded as determined by CEX-HPLC. There was increased degradation observed following incubation at 45° C. for 8 weeks as determined by SE-HPLC and CEX-HPLC indicating that aggregate and charge variant formation are the main degradation routes for the mAb1 antibody molecule. No degradation was observed when the formulated mAb1 antibody was stored for 6 months at 5° C.

TABLE 7

| | mAb1 (mg/ml) | Histidine (mM) | Acetate (mM) | Arginine (mM) | NaCl (mM) | Sucrose (% w/v) | pH | Viscosity (cPois.) | Osmolality (mOsm/kg) |
|---|---|---|---|---|---|---|---|---|---|
| A | 150 | 20 | 12.5 | 25 | 0 | 5 | 5.9 | 8.5 | 293 |
| B | 150 | 20 | 12.5 | 0 | 0 | 10 | 5.9 | 11 | 448 |
| C | 175 | 20 | 12.5 | 100 | 0 | 1 | 5.9 | ~8.0 | ~290 |
| D | 175 | 20 | 12.5 | 50 | 0 | 5 | 5.9 | ~9.5 | ~370 |
| E | 175 | 20 | 12.5 | 0 | 0 | 10 | 5.9 | ~20 | ~440 |
| F | 200 | 20 | 12.5 | 100 | 0 | 1 | 5.9 | ~15 | ~290 |
| G | 200 | 20 | 12.5 | 0 | 100 | 5 | 5.9 | ~19.2 | ~430 |
| H | 200 | 20 | 12.5 | 100 | 0 | 5 | 5.9 | ~17 | ~430 |
| I | 200 | 20 | 12.5 | 50 | 0 | 5 | 5.9 | ~18 | ~330 |
| J | 200 | 20 | 12.5 | 25 | 0 | 5 | 5.9 | ~23 | ~290 |
| K | 200 | 20 | 12.5 | 0 | 0 | 10 | 5.9 | ~35 | ~440 |

(w/v) sucrose, 0.2% (w/v) Polysorbate 20, and 150 mg/ml mAb1, at pH 5.9 (Formulation A) represents an optimized formulation having a low viscosity (about 8.5 cPoise) and being physiologically isotonic (about 293 mOsm/kg), while maintaining the stability of mAb1.

Example 5. Characterization of Formulation A

The main degradation pathways identified during the development of the mAb1 liquid formulation were the formation of aggregates, cleavage products, and charge variants. The formation of these degradation products was minimized by formulating mAb1 in a formulation containing 20 mM histidine, 12.5 mM acetate, 0.2% polysorbate 20, 5% sucrose and 25 mM L-arginine hydrochloride at pH 5.9. The formulated 150 mg/ml mAb1 was observed to be clear to slightly opalescent liquid solution, essentially free from visible particles.

The formulated mAb1 was physically and chemically stable when subjected to various stress (25° C. and 45° C. incubation) and real-time storage condition (5° C.) (Table 8). The appearance was unaffected when the mAb1 was incubated at 25° C. (3 months) or stored at 5° C. for 6 months.

According to Table 8, OD=Optical density; RP-HPLC=Reversed phase high performance liquid chromatography; SE-HPLC=Size exclusion high performance liquid chromatography; and CEX-HPLC=Cation exchange high performance liquid chromatography. Acidic or basic species are defined as the sum of mAb1 peaks that elute from the CEX-HPLC column with earlier or later retention times than the main peak, respectively.

Example 6. Containers

Formulations containing mAb1 have been determined to be stable when filter sterilized. A Millipore MILLIPAK filtration unit was used in the manufacturing of the clinical supplies while a filter of identical composition was used in the research studies (Millipore MILLEX DURAPORE).

A 5-mL glass vial was filled with a minimum of 2.5 mL 150 mg/ml mAb1, 5% (w/v) sucrose, 25 mM L-arginine hydrochloride, 0.2% (w/v) polysorbate 20, 12.5 mM acetate, 20 mM histidine, pH 5.9. An overage of 0.5 mL of formulation was applied in the 5-mL vial to ensure that 2.0 mL of the formulation could be withdrawn. This overage was not designed to compensate for losses during manufacture of the mAb1 or formulation containing the mAb1, degradation during manufacture, degradation during storage (shelf life), or to extend the expiration dating period.

Compared to storage in glass vials, the stability of the formulated mAb1 (Formulation A) was not affected when stored in a either a polypropylene tube, a polystyrene tube, a polycarbonate tube, or in a glass vial containing pieces of stainless steel (Table 9).

TABLE 8

| Stress Test | No Storage | 5° C. | | | 25° C. | |
|---|---|---|---|---|---|---|
| Length of Storage | — | 2 mo. | 3 mo. | 6 mo. | 1 mo. | 3 mo. |
| Visual Appearance | Pass | Pass | Pass | Pass | Pass | Pass |
| Turbidity (OD 405 nm) | 0.00 | 0.00 | 0.00 | 0.00 | 0.01 | 0.01 |
| pH | 6.0 | 6.0 | 5.9 | 5.9 | 6.0 | 6.0 |
| % mAb1 (RP-HPLC) | 100 | 97 | 104 | | 97 | 102 |
| % Native mAb1 (SE-HPLC) | 98.1 | 98.2 | 98.2 | | 98.1 | 97.8 |
| % mAb1        Acidic | 14.6 | 14.7 | 14.7 | | 16.0 | 17.6 |
| (Peaks from   Main Peak | 70.7 | 70.5 | 70.4 | | 69.8 | 67.4 |
| CEX-HPLC)     Basic | 14.7 | 14.8 | 14.9 | | 14.3 | 15.0 |

| Stress Test | No Storage | 45° C. | | |
|---|---|---|---|---|
| Length of Storage | — | 2 wk | 4 wk | 8 wk |
| Visual Appearance | Pass | Pass | Pass | Pass |
| Turbidity (OD 405 nm) | 0.00 | 0.02 | 0.03 | 0.05 |
| pH | 6.0 | 6.0 | 6.0 | 6.0 |
| % mAb1 (RP-HPLC) | 100 | 102 | 98 | 100 |
| % Native mAb1 (SE-HPLC) | 98.1 | 95.9 | 94.2 | 90.5 |
| % mAb1        Acidic | 14.6 | 20.8 | 29.9 | 44.0 |
| (Peaks from   Main Peak | 70.7 | 64.5 | 56.7 | 45.1 |
| CEX-HPLC)     Basic | 14.7 | 14.7 | 13.4 | 10.9 |

According to Table 9, 150 mg/ml mAb1, 5% Sucrose, 25 mM Arginine Hydrochloride, 0.2% PS-20, 20 mM Histidine, 12.5 mM Acetate, pH 5.9 was incubated with/in various materials at 40° C. for 14 days. OD=Optical density; RP-HPLC=Reversed phase high performance liquid chromatography; SE-HPLC=Size exclusion high performance liquid chromatography; and CEX-HPLC=Cation exchange high performance liquid chromatography. Turbidity is reported as the relative change in OD at 405 nm as compared to the starting material. Acidic or basic species are defined as the sum of mAb1 peaks that elute from the CEX-HPLC column with earlier or later retention times than the main peak, respectively.

TABLE 9

| Storage Temperature | No Storage | 40° C. for 14 days | | | | |
|---|---|---|---|---|---|---|
| Storage Container | Glass | Glass | Poly-propylene | Poly-styrene | Poly-carbonate | Stainless Steel |
| Visual Appearance | Pass | Pass | Pass | Pass | Pass | Pass |
| Turbidity (OD at 405 nm) | 0.00 | 0.01 | 0.01 | 0.02 | 0.02 | 0.01 |
| pH | 5.9 | 5.9 | 5.7 | 5.8 | 5.8 | 5.9 |
| % mAb1 (RP-HPLC) | 100 | 102 | 103 | 107 | 106 | 102 |
| % Native mAb1 (SE-HPLC) | 98.4 | 97.6 | 97.4 | 97.5 | 97.5 | 96.1 |
| % Peak        Acidic | 14.8 | 18.4 | 19.1 | 18.4 | 18.4 | 20.3 |
| mAb1          Main Peak | 70.7 | 65.8 | 65.5 | 66.0 | 66.5 | 65.0 |
| (CEX-HPLC)    Basic | 14.5 | 15.8 | 15.3 | 15.6 | 15.1 | 14.7 |

TABLE 10

| Sequences Excluded from ST.26-Formatted Sequence Listing | |
|---|---|
| SEQ ID NO: | Sequence |
| 7 | LGS |
| 15 | VAS |
| 23 | AAS |

What is claimed is:

1. A pharmaceutical formulation comprising:

(i) an anti-human interleukin-4 receptor alpha (anti-hIL4Rα) antibody at a concentration of about 100 mg/ml to about 200 mg/ml, wherein the anti-hIL4Rα antibody is a human antibody, wherein the anti-hIL4Rα antibody is an immunoglobulin molecule comprising two heavy chains and two light chains interconnected by disulfide bonds, wherein each heavy chain comprises a heavy chain variable region (HCVR), wherein the HCVR comprises the amino acid sequence of SEQ ID NO: 1, wherein each light chain comprises a light chain variable region (LCVR), wherein the LCVR comprises the amino acid sequence of SEQ ID NO: 5;

(ii) a thermal stabilizer at a concentration from about 0.9%±0.135% w/v to about 10%±1.5% w/v;

(iii) a non-ionic surfactant; and (iv) arginine at a concentration from about 20 to 100 mM;

wherein the pharmaceutical formulation has a pH from about 5.6 to about 6.2;

wherein the viscosity of the pharmaceutical formulation is less than 35 cPoise; and wherein less than about 5% of the anti-hIL4Rα antibody recovered from the pharmaceutical formulation after 3 months of storage at 5° C. is aggregated, as determined by size exclusion chromatography.

2. The pharmaceutical formulation of claim 1, wherein the non-ionic surfactant is a poloxamer or a polyethylene glycol.

3. The pharmaceutical formulation of claim 2, wherein the non-ionic surfactant is poloxamer 188.

4. The pharmaceutical formulation of claim 1, wherein the non-ionic surfactant is a polysorbate.

5. The pharmaceutical formulation of claim 4, wherein the polysorbate is polysorbate 20 or polysorbate 80.

6. The pharmaceutical formulation of claim 5, wherein the polysorbate 20 or polysorbate 80 is at a concentration of about 0.2% w/v.

7. The pharmaceutical formulation of claim 5, wherein the pharmaceutical formulation has a pH of about 5.9.

8. The pharmaceutical formulation of claim 5, wherein the anti-hIL4Rα antibody is at a concentration of about 175 mg/mL.

9. The pharmaceutical formulation of claim 8, wherein the arginine is at a concentration of about 50 mM±7.5 mM.

10. The pharmaceutical formulation of claim 5, wherein the anti-hIL4Rα antibody is at a concentration of about 150 mg/mL.

11. The pharmaceutical formulation of claim 10, wherein the arginine is at a concentration of about 50 mM±7.5 mM.

12. The pharmaceutical formulation of claim 1, wherein the pharmaceutical formulation has an osmolality of less than about 450 mOsm/kg.

13. The pharmaceutical formulation of claim 1, wherein the thermal stabilizer is a sugar or a sugar alcohol at a concentration from about 2.5% w/v to about 10% w/v.

14. The pharmaceutical formulation of claim 13, wherein the sugar or sugar alcohol is sucrose, sorbitol, mannitol, or trehalose.

15. The pharmaceutical formulation of claim 14, wherein the sugar or sugar alcohol is sucrose.

16. The pharmaceutical formulation of claim 15, wherein the sucrose is at a concentration of about 5%±0.75% w/v.

17. The pharmaceutical formulation of claim 15, wherein the sucrose is at a concentration of about 5.5%±0.825% w/v.

18. The pharmaceutical formulation of claim 14, wherein the pharmaceutical formulation has an osmolality of less than about 450 mOsm/kg.

19. The pharmaceutical formulation of claim 14, wherein the non-ionic surfactant is a poloxamer or a polyethylene glycol.

20. The pharmaceutical formulation of claim 19, wherein the non-ionic surfactant is poloxamer 188.

21. The pharmaceutical formulation of claim 14, wherein the non-ionic surfactant is a polysorbate.

22. The pharmaceutical formulation of claim 21, wherein the polysorbate is polysorbate 20 or polysorbate 80.

23. The pharmaceutical formulation of claim 22, wherein the polysorbate 20 or polysorbate 80 is at a concentration of about 0.2% w/v.

24. The pharmaceutical formulation of claim 23, wherein the pharmaceutical formulation has a pH of about 5.9.

25. The pharmaceutical formulation of claim 22, wherein the anti-hIL4Rα antibody is at a concentration of about 175 mg/mL.

26. The pharmaceutical formulation of claim 25, wherein the arginine is at a concentration of about 50 mM±7.5 mM.

27. The pharmaceutical formulation of claim 25, wherein the non-ionic surfactant is polysorbate 80, and wherein the polysorbate 80 is at a concentration of about 0.2% w/v.

28. The pharmaceutical formulation of claim 22, wherein the anti-hIL4Rα antibody is at a concentration of about 150 mg/mL.

29. The pharmaceutical formulation of claim 28, wherein the arginine is at a concentration of about 50 mM±7.5 mM.

30. The pharmaceutical formulation of claim 28, wherein the non-ionic surfactant is polysorbate 80, and wherein the polysorbate 80 is at a concentration of about 0.2% w/v.

* * * * *

SEQUENCE LISTING

Sequence total quantity: 26
SEQ ID NO: 1                moltype = AA  length = 124
FEATURE                     Location/Qualifiers
source                      1..124
                            mol_type = protein
                            organism = Homo sapiens
SEQUENCE: 1
EVQLVESGGG LEQPGGSLRL SCAGSGFTFR DYAMTWVRQA PGKGLEWVSS ISGSGGNTYY     60
ADSVKGRFTI SRDNSKNTLY LQMNSLRAED TAVYYCAKDR LSITIRPRYY GLDVWGQGTT    120
VTVS                                                                124

SEQ ID NO: 2                moltype = AA  length = 8
FEATURE                     Location/Qualifiers
source                      1..8
                            mol_type = protein
                            organism = Homo sapiens
SEQUENCE: 2
GFTFRDYA                                                              8

SEQ ID NO: 3                moltype = AA  length = 8
FEATURE                     Location/Qualifiers
source                      1..8
                            mol_type = protein
                            organism = Homo sapiens
SEQUENCE: 3
ISGSGGNT                                                              8

SEQ ID NO: 4                moltype = AA  length = 16
FEATURE                     Location/Qualifiers
source                      1..16
                            mol_type = protein
                            organism = Homo sapiens
SEQUENCE: 4
AKDRLSITIR PRYYGL                                                    16

SEQ ID NO: 5                moltype = AA  length = 112
FEATURE                     Location/Qualifiers
source                      1..112
                            mol_type = protein
                            organism = Homo sapiens
SEQUENCE: 5
DIVMTQSPLS LPVTPGEPAS ISCRSSQSLL YSIGYNYLDW YLQKSGQSPQ LLIYLGSNRA     60
SGVPDRFSGS GSGTDFTLKI SRVEAEDVGF YYCMQALQTP YTFGQGTKLE IK            112

SEQ ID NO: 6                moltype = AA  length = 11
FEATURE                     Location/Qualifiers
source                      1..11
                            mol_type = protein
                            organism = Homo sapiens
SEQUENCE: 6
QSLLYSIGYN Y                                                         11

SEQ ID NO: 7                moltype =   length =
SEQUENCE: 7
000

SEQ ID NO: 8                moltype = AA  length = 9
FEATURE                     Location/Qualifiers
source                      1..9
                            mol_type = protein
                            organism = Homo sapiens
SEQUENCE: 8
MQALQTPYT                                                            9

SEQ ID NO: 9                moltype = AA  length = 118
FEATURE                     Location/Qualifiers
source                      1..118
                            mol_type = protein
                            organism = Homo sapiens
SEQUENCE: 9
EVQLVESGGG LVQPGRSLRL SCEASGFTFD DYAMHWVRQA PGKGLEWVSG LSRTSVSIGY     60
ADSVKGRFTI SRDNAKNSLY LEMNSLRPED TALYYCAKWG TRGYFDYWGQ GTLVTVSS     118

SEQ ID NO: 10               moltype = AA  length = 8
FEATURE                     Location/Qualifiers
source                      1..8
                            mol_type = protein
                            organism = Homo sapiens

```
SEQUENCE: 10
GFTFDDYA                                                                  8

SEQ ID NO: 11          moltype = AA  length = 8
FEATURE                Location/Qualifiers
source                 1..8
                       mol_type = protein
                       organism = Homo sapiens
SEQUENCE: 11
LSRTSVSI                                                                  8

SEQ ID NO: 12          moltype = AA  length = 11
FEATURE                Location/Qualifiers
source                 1..11
                       mol_type = protein
                       organism = Homo sapiens
SEQUENCE: 12
AKWGTRGYFD Y                                                              11

SEQ ID NO: 13          moltype = AA  length = 107
FEATURE                Location/Qualifiers
source                 1..107
                       mol_type = protein
                       organism = Homo sapiens
SEQUENCE: 13
DIQMTQSPSS VSASVGDRVT ITCRASQDIS IWLAWYQQSP GKAPKLLINV ASRLQSGVPS         60
RFSGSGSGTD FTLTINSLQP EDFVTYYCQQ ANSFPITFGQ GTRLEIK                       107

SEQ ID NO: 14          moltype = AA  length = 6
FEATURE                Location/Qualifiers
source                 1..6
                       mol_type = protein
                       organism = Homo sapiens
SEQUENCE: 14
QDISIW                                                                    6

SEQ ID NO: 15          moltype =   length =
SEQUENCE: 15
000

SEQ ID NO: 16          moltype = AA  length = 9
FEATURE                Location/Qualifiers
source                 1..9
                       mol_type = protein
                       organism = Homo sapiens
SEQUENCE: 16
QQANSFPIT                                                                 9

SEQ ID NO: 17          moltype = AA  length = 117
FEATURE                Location/Qualifiers
source                 1..117
                       mol_type = protein
                       organism = Homo sapiens
SEQUENCE: 17
QVQLVESGGG VVQPGRSLRL SCAASGFTFR SYGMHWVRQA PGKGLEWVAV ISYDGSNKYY         60
IDSVKGRFTI SRDNSKNTLN LQMNSLRLED TAVYYCAKEG RGGFDYWGQG TLVTVSS            117

SEQ ID NO: 18          moltype = AA  length = 8
FEATURE                Location/Qualifiers
source                 1..8
                       mol_type = protein
                       organism = Homo sapiens
SEQUENCE: 18
GFTFRSYG                                                                  8

SEQ ID NO: 19          moltype = AA  length = 8
FEATURE                Location/Qualifiers
source                 1..8
                       mol_type = protein
                       organism = Homo sapiens
SEQUENCE: 19
ISYDGSNK                                                                  8

SEQ ID NO: 20          moltype = AA  length = 10
FEATURE                Location/Qualifiers
source                 1..10
                       mol_type = protein
                       organism = Homo sapiens
SEQUENCE: 20
```

-continued

```
AKEGRGGFDY                                                              10

SEQ ID NO: 21               moltype = AA  length = 107
FEATURE                     Location/Qualifiers
source                      1..107
                            mol_type = protein
                            organism = Homo sapiens
SEQUENCE: 21
DIQMTQSPSS LSASVGDRVT ITCRASQVIN NYLAWFQQKP GKVPKSLIHA ASSLQSGVPS  60
KFSGSGSGTD FTLTISSLQP EDFATYYCQQ YNSHPWTFGQ GTKVEIK                107

SEQ ID NO: 22               moltype = AA  length = 6
FEATURE                     Location/Qualifiers
source                      1..6
                            mol_type = protein
                            organism = Homo sapiens
SEQUENCE: 22
QVINNY                                                                  6

SEQ ID NO: 23               moltype =    length =
SEQUENCE: 23
000

SEQ ID NO: 24               moltype = AA  length = 9
FEATURE                     Location/Qualifiers
source                      1..9
                            mol_type = protein
                            organism = Homo sapiens
SEQUENCE: 24
QQYNSHPWT                                                               9

SEQ ID NO: 25               moltype = AA  length = 825
FEATURE                     Location/Qualifiers
source                      1..825
                            mol_type = protein
                            organism = Homo sapiens
SEQUENCE: 25
MGWLCSGLLF PVSCLVLLQV ASSGNMKVLQ EPTCVSDYMS ISTCEWKMNG PTNCSTELRL  60
LYQLVFLLSE AHTCIPENNG GAGCVCHLLM DDVVSADNYT LDLWAGQQLL WKGSFKPSEH  120
VKPRAPGNLT VHTNVSDTLL LTWSNPYPPD NYLYNHLTYA VNIWSENDPA DFRIYNVTYL  180
EPSLRIAAST LKSGISYRAR VRAWAQCYNT TWSEWSPSTK WHNSYREPFE QHLLLGVSVS  240
CIVILAVCLL CYVSITKIKK EWWDQIPNPA RSRLVAIIIQ DAQGSQWEKR SRGQEPAKCP  300
HWKNCLTKLL PCFLEHNMKR DEDPHKAAKE MPFQGSGKSA WCPVEISKTV LWPESISVVR  360
CVELFEAPVE CEEEEEVEEE KGSFCASPES SRDDFQEGRA GIVARLTESL FLDLLGEENG  420
GFCQQDMGES RLLPPSGSTS AHMPWDEFPS AGPKEAPPWG KEQPLHLEPS PPASPTQSPD  480
NLTCTETPLV IAGNPAYRSF SNPLSQSPCP RELGPDPLLA RHLEEVEPEM PCVPQLSEPT  540
TVPQPEPETW EQILRRNVLQ HGAAAAPVSA PTSGYREFVH AVEQGGTQAS AVVGLGPPGE  600
AGYKAFSSLL ASSAVSPEKC GFGASSGEEG YKPFQDLIPG CPGDPAPVPV PLFTFGLDRE  660
PPRSPQSSHL PSSSPEHLGL EPGEKVEDMP KPPLPQEQAT DPLVDSLGSG IVYSALTCHL  720
CGHLKQCHGQ EDGGQTPVMA SPCCGCCCGD RSSPPTTPLR APDPSPGGVP LEASLCPASL  780
APSGISEKSK SSSSFHPAPG NAQSSSQTPK IVNFVSVGPT YMRVS                  825

SEQ ID NO: 26               moltype = AA  length = 207
FEATURE                     Location/Qualifiers
source                      1..207
                            mol_type = protein
                            organism = Homo sapiens
SEQUENCE: 26
MKVLQEPTCV SDYMSISTCE WKMNGPTNCS TELRLLYQLV FLLSEAHTCI PENNGGAGCV  60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQH                                      207
```